(12) United States Patent
Pappolla et al.

(10) Patent No.: US 6,395,768 B1
(45) Date of Patent: May 28, 2002

(54) USES FOR INDOLE-3-PROPIONIC ACIDS AND SALTS AND ESTERS THEREOF

(75) Inventors: Miguel A. Pappolla, Mobile, AL (US); Blas Frangione, New York; Jorge Ghiso, Elmhurst, both of NY (US); Burkhard Poeggeler, Goettingen (DE)

(73) Assignees: South Alabama Medical Science Foundation, Mobile, AL (US); New York University, New York, NY (US)

( * ) Notice: Subject to any disclaimer, the term of this patent is extended or adjusted under 35 U.S.C. 154(b) by 0 days.

(21) Appl. No.: 09/580,437

(22) Filed: May 30, 2000

Related U.S. Application Data

(63) Continuation of application No. 09/256,448, filed on Feb. 23, 1999, now abandoned
(60) Provisional application No. 60/075,555, filed on Feb. 23, 1998, and provisional application No. 60/112,565, filed on Dec. 16, 1998.

(51) Int. Cl.$^7$ .................. A61K 31/405; A61K 31/40
(52) U.S. Cl. .................. 514/415; 514/416; 514/418; 514/419
(58) Field of Search ................. 514/415, 416, 514/418, 419

(56) References Cited

U.S. PATENT DOCUMENTS 6,040,331 A * 3/2000 Yamamoto et al. ......... 514/411

OTHER PUBLICATIONS

Behl et al, "Vitamin E Protects Nerve Cells from Amyloid β Protein Toxicity", *Biochem Biophys Res Comm* 186(2):944–950 (1992).
Kemp et al, *Organic Chemistry*, Worth Publishers, New York, NY, pp. 371–377 and 1258 (1980).
Robakis et al, "Involvement of amyloid as a central step in the development of Alzheimer's disease", *Neurobiol Aging.* 15 Suppl 2:S127–129 (1994).
Guidetti et al, "Antioxidant Effects of Indole–3–Propionic Acid", *Soc Neuroscience* 24:1494 (Abstract 584.14) (1998).
Chyan et al., "Neuroprotective Activity of Melatonin Against Alzheimer –Amyloid is not Mediatede by Melatonin", *Society for Neuroscience Abst.*, vol. 24, No. 1–2, (1998).
Poeggler et al., "Indole–3–propionate: a potent hydroxyl radical scavenger in rat brain", *Brain Research* vol. 815, pp. 382–388, (1999).
Medvedev et al., "Monoamine Oxidase A–inhibiting components urinary tribulin: purification and indentification", *Journal of Neural Transmission*, vol. 9, pp. 225–237, (1995).
Matuszak et al., "Reaction of Melatonin and related indoles with hydroxyl Radicals: EPR and Spin Trapping Investigation", *Free Radic. Biol. Med.*, vol. 23, pp. 367–372, (1997).

* cited by examiner

*Primary Examiner*—Theodore J. Criares
(74) *Attorney, Agent, or Firm*—Browdy and Neimark, P.L.L.C.

(57) ABSTRACT

The cytotoxic effects of amyloid beta protein on cells are prevented by contacting the cells with an effective amount of an indole-3-propionic acid or a salt or ester thereof. Furthermore, a fibrillogenic disease can be treated in a human subject by administering to the human subject an amount of-an indole-3-propionic acid or a salt or ester thereof effective to prevent or reverse fibrillogenesis. Oxidation in a biological sample can be decreased by contacting the biological sample with an effective amount of an indole-3-propionic acid or a salt or ester thereof. Additionally, diseases or other conditions where free radicals and/or oxidative stress play a role can be treated by administering an effective amount of an indole-3-propionic acid or a salt or ester thereof.

19 Claims, 3 Drawing Sheets

USES FOR INDOLE-3-PROPIONIC ACIDS AND SALTS AND ESTERS THEREOF

The present application is a continuation of U.S. application Ser. No. 09/256,448, filed Feb. 23, 1999, now abandoned.

The present application claims priority from U.S. Provisional Patent Application Ser. No. 60/075,555, filed Feb. 23, 1998, and from U.S. Provisional Patent Application Ser. No. 60/112,565, filed Dec. 16, 1998. The entire contents of these two provisional applications are hereby incorporated by reference.

Throughout this application, various publications are referenced, many in parenthesis. Full citations for these publications are provided at the end of each part of the application. The disclosures of these publications in their entireties are hereby incorporated by reference in this application.

The subject matter of this application was made with support from the United States Government (National Institutes of Health Grant No. AG11130). The government may have certain rights in this application.

FIELD OF THE INVENTION

The present invention relates to a use of indole-3-propionic acid and, more particularly, to the use of indole-3-propionic acid to prevent cytotoxic effects of amyloid beta protein, to treat fibrillogenic diseases, to decrease oxidation in biological samples, and to treat diseases or other conditions where free radicals and/or oxidative stress play a role.

BACKGROUND OF THE INVENTION

It is estimated that ten percent of persons older than 65 years of age have mild to severe dementia. Alzheimer's Disease ("AD") is the most common cause of chronic dementia with approximately two million people in the United States having the disease. Although once considered a condition of middle age, it is now known that the histopathologic lesions of Alzheimer'Disease (i.e., neuritic amyloid plaques, neurofibrillary degeneration, and granulovascular neuronal degeneration) are also found in the brains of elderly people with dementia. The number of such lesions correlates with the degree of intellectual deterioration. This high prevalence, combined with the rate of growth of the elderly segment of the population, make dementia (and particularly AD) one of the most important current public health problems.

Deposition of cerebral amyloid is a primary neuropathologic marker of Alzheimer'Disease. The amyloid is composed of a 40–42 amino acid peptide called the amyloid beta protein ("A$\beta$") (Glenner and Wong, 1984). Amyloid deposits in AD are found mainly as components of senile plaques, and in the walls of cerebral and meningeal blood vessels (Robakis and Pangalos, 1994).

Molecular cloning showed that AP comprises a small region of a larger amyloid precursor protein ("APP") (Robakis et al., 1987; Weidemann et al., 1989). Briefly, this is a type I integral membrane glycoprotein having a large extracytoplasmic portion, a smaller intracytoplasmic region, and a single transmembranous domain. APP undergoes extensive post-translational modifications (Pappolla and Robakis, 1995; Robakis and Pangalos, 1994) prior-to the secretion of its N-terminal portion (Sambamurti et al., 1992; Robakis and Pangalos, 1994). Physiologic processing of APP involves cleavage within the A$\beta$ sequence by an unidentified enzyme, alpha-secretase (Anderson et al., 1991). Smaller quantities of APP molecules are cleaved at two other sites that could potentially produce amyloidogenic secreted or membrane bound APP (Robakis and Pangalos, 1994). A$\beta$ is also produced during normal cellular metabolism (Haass et al., 1992; Shoji et al., 1992).

There is some controversy as to whether amyloid causes AD; however, three main lines of evidence have strengthened the amyloid hypothesis. The first piece of evidence is provided by the identification of several point mutations within the APP gene. These mutations segregate within a subgroup of patients afflicted with a familial form of the disorder and thus suggest a pathogenetic relationship between the APP gene and AD (Chartier-Harlin et al., 1991; Kennedy et al., 1993). Secondly, amyloid deposition temporally precedes the development of neurofibrillary changes (Pappolla et al., 1996) and this observation is also consistent with a link between amyloid and neuronal degeneration. Finally, it has been shown that A$\beta$ is toxic to neurons (Yankner et al., 1990; Behl et al., 1992; Behl et al., 1994; Zhang et al., 1994), a finding that also strengthened the hypothesis that the amyloid peptide may contribute to the neuronal pathology in AD.

The finding that A$\beta$ has neurotoxic properties has provided a possible connection between amyloid accumulation and neurodegeneration. Because of the close association between aging and AD and the similarities in the neuropathology of both conditions, oxidative stress has been proposed to play a role in the pathogenesis of AD lesions.

Several investigators demonstrated that oxygen free-radicals ("OFRs") are related to the cytotoxic properties of A$\beta$ (Behl, 1992; Behl, 1994; Harris et al., 1995; Butterfield et al., 1994; Goodman and Mattson, 1994). Such findings are important, since markers of oxidative injury are topographically associated with the neuropathologic lesions of AD (Pappolla et al., 1992; Furuta et al., 1995; Smith et al., 1995; Pappolla et al., 1996). Because of these observations, antioxidants have been proposed as potential therapeutic agents in AD (Mattson, 1994; Hensley et al., 1994; Pappolla et al., 1996).

A need continues for methods of treating AD and other fibrillogenic diseases.

SUMMARY OF THE INVENTION

The present invention relates to a method of preventing cytotoxic effects of amyloid beta protein on cells. The method includes contacting the cells with an effective amount of an indole-3-propionic acid or an ester or salt thereof.

The present invention further relates to a method of treating a fibrillogenic disease in a human subject. The method includes administering, to the human subject, an amount of indole-3-propionic acid or an ester or salt thereof effective to inhibit or reverse fibrillogenesis.

The present invention also relates to a method of decreasing oxidation in a biological sample. The method includes contacting the biological sample with an effective amount of a indole-3-propionic acid or a salt or ester thereof.

The present invention still further relates to a method of treating diseases or other conditions where free radicals and/or oxidative stress play a role. The method includes administering, to the human subject, an amount of indole-3-propionic acid or an ester or salt thereof effective to treat such disease or condition.

DETAILED DESCRIPTION OF THE INVENTION

Figure 1:
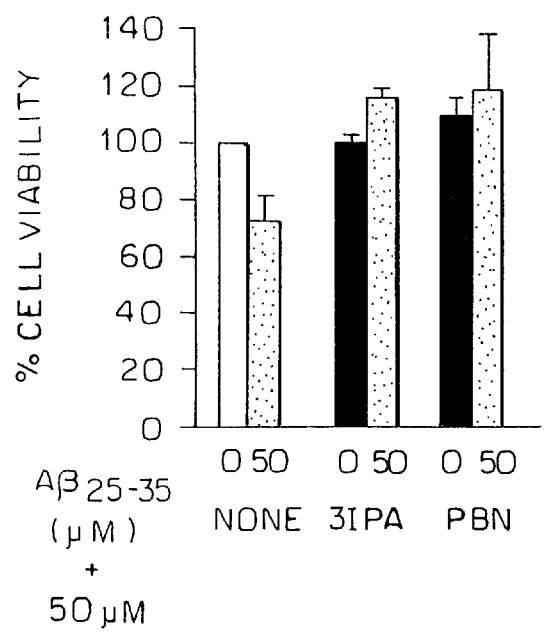
FIG. 1 is a bar graph illustrating viabilities expressed as percentages using SK-N-SH human neuroblastoma cells exposed to either A$\beta$(25–35) alone or in conjunction with IPA or PBN.

The present invention is based on the discovery that the natural compound indole-3-propionic acid ("IPA") has a combination of properties which render it particularly useful for preventing the cytotoxic effects of amyloid beta protein on cells, for treating any fibrillogenic disease, and for protecting cells from oxidative damage. Accordingly, the compounds of the present invention are powerful therapeutic agents in Alzheimer's Disease and other fibrillogenic diseases, such as, without limitation, prion-related diseases. It may also be used as a therapeutic agent for the treatment of other diseases where free radicals and/or oxidative stress plays a role. These conditions include Parkinson's Disease, Lewy body dementia, amyotrophic lateral sclerosis, progressive supranuclear palsy, other forms of amyloidoses, stroke, atherosclerosis, emphysema, and some forms of cancer. Furthermore, data show that IPA also has antifibrillogenic activity.

The subject invention provides a method of preventing cytotoxic effects of amyloid beta protein on cells. The method comprises exposing the cells to an effective amount of an indole-3-propionic acid or a salt or ester thereof.

As used herein, "amyloid beta protein" ("Aβ") refers to the 40–42 amino acid peptide that makes up the cerebral amyloid which is the primary neuropathologic marker of Alzheimer's Disease ("AD"), and refers to fragments of the Aβ capable of causing cytotoxic effects on cells. For example, one such fragment of Aβ is the fragment made of up amino acid residues 25–35 of Aβ (see Glenner and Wong 1984 for the full amino acid sequence of Aβ, which is hereby incorporated by reference).

As used herein, indole-3-propionic acids are meant to include compounds having the formula:

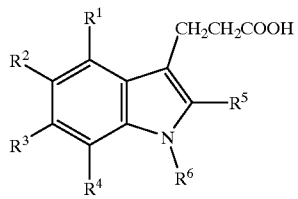

where $R^1$, $R^2$, $R^3$, $R^4$, $R^5$, and $R^6$ are independently selected from the group consisting of hydrogen, substituted alkyl groups, unsubstituted alkyl groups, substituted aryl groups, unsubstituted aryl groups, alkoxy groups, substituted or unsubstituted amino groups, thiol groups, alkylthio groups, arylthio groups, and the like. Preferably, $R^5$ and $R^6$ are hydrogen. One example of a suitable indole-3-propionic acid is indole-3-propionic acid, which has the above formula where each of $R^1$, $R^2$, $R^3$, $R^4$, $R^5$, and $R^6$ is a hydrogen atom. Preferred substituents are those which do not significantly affect the antioxidant and antifibrillogenic properties of the indole-3-propionic acids, as described in more detail below. Other preferred substituents are those which enhance brain-penetration, such as a covalently bonded lipophilic moiety. These substituents can be present on any atom of the indole nucleus which has an available hydrogen. The mode of attachment of the lipophilic moiety is not critical, and can be effected by a carbon-carbon, carbon-oxygen, carbon-nitrogen, or carbon-sulfur bond. To maximize the lipophilicity of the resulting compound, however, it is preferred that attachment be effected so as to minimize polarity. Consequently, it is preferred that the lipophilic moiety be attached via a carbon-carbon bond. The lipophilic moiety can be a hydrocarbon, such as an alkyl having from 5 to 20 carbons. These alkyls can be unsubstituted, such as hexyl or dodecyl, or substituted, such as with an aryl moiety, as in the case where the substituted alkyl is a benzyl or a phenylethyl group. Alternatively, the lipophilic moiety can be substituted or unsubstituted homocyclic rings, such as phenyl groups or a tolyl groups, homocyclic ring systems, heterocyclic rings, heterocyclic ring systems, or multicyclic lipophilic "cage" moieties, such as adamantane. In particular, the use of the multicyclic "cage" compounds are particularly advantageous (Tsuzuki, 1991).

Some indole-3-propionic acids can be obtained commercially. Others can be prepared by modifications to conventional procedures for the preparation of indole-3-propionic acid, such as the ones described in Johnson and Crosby, 1969) and in U.S. Pat. No. 5,300,506, U.S. Pat. No. 5,077, 293, and JP 03/127,732, each of which are hereby incorporated by reference.

As indicated above, the present invention can also be carried out using salts of the above-described indole-3-propionic acids. Suitable salts include, for example, pharmaceutically acceptable salts, such as sodium salts, potassium salts, and ammonium salts. Salts of indole-3-propionic acid can be made by conventional methods from the corresponding indole-3-propionic acid by mixing the an aqueous solution or dispersion of the acid with an appropriate base (e.g., sodium, potassium, or ammonium hydroxide, or sodium or potassium carbonate).

In addition, also as indicated above, the present invention can be carried out using esters of the above-described indole-3-propionic acids. Examples of such esters include methyl ester, ethyl ester, propyl-ester, benzyl ester, and the like. Indole-3-propionic acid esters bearing a lipophilic ester moiety, such as those described above, can also be used advantageously to increase the brain penetration of the indole-3-propionic acid ester. Indole-3-propionic acid esters can be prepared from their corresponding acids or salts by a variety of methods known to those skilled in the art, such as, for example, by first transforming the acid to the acid chloride and then reacting the acid chloride with a suitable alcohol. Other suitable methods for making esters are described in Kemp and Vellaccio, 1980.

Preferably, the indole-3-propionic acid, salt, or ester has antioxidative and/or antifibrillogenic properties and/or prevents the cytotoxic effects of Aβ. Various indole-3-propionic acids, salts, and esters can readily be assayed to ensure that the function of preventing the cytotoxic effects of Aβ is retained using the methodology disclosed herein, such as assays for cell viability, lipid peroxidation, intracellular $Ca^{2+}$, and oxygen free-radicals. The prevention of other cytotoxic effects of Aβ on cells can readily be observed microscopically, such as the prevention of membrane blebbing, cell retraction, abnormal distribution of chromatin, and karyorrhexis. Antioxidation and antifibrillogenic effects of the various indole-3-propionic acids can be assayed by conventional methods, such as those described in the Examples of this application.

As indicated above, the cytotoxic or cell killing effects of Aβ include, for example, decreased cell viability (i.e., cell death), increased lipid peroxidation (an indicator of increased oxygen free-radicals), increased intracellular $Ca^{2+}$ levels, diffuse membrane blebbing, cell retraction, abnormal distribution of chromatin towards the nuclear membrane, and karyorrhexis.

The cytotoxic effects of Aβ are most readily seen in neuronal cells (including cells of the central and peripheral nervous systems), and occur in human subjects afflicted with fibrillogenic diseases, such as Alzheimer's Disease.

The effective amount of the indole-3-propionic acid (or salt or ester thereof) for prevention of the cytotoxic effects of Aβ can be readily determined by conventional methods known in the art, such as establishing dose-response curves, as described below. It will be appreciated that the actual preferred amount of the indole-3-propionic acid (or salt or ester thereof) to be administered according to the present invention will vary according to the particular form of the indole-3-propionic acid (i.e., whether it is a salt, an ester, or an-acid), the particular composition formulated, and the mode of administration. Many factors that may modify the action of the indole-3-propionic acid (or salt or ester thereof) can be taken into account by those skilled in the art; e.g., body weight, sex, diet, time of administration, route of administration, rate of excretion, condition of the subject, drug combinations, and reaction sensitivities and severities. Administration can be carried out continuously-or periodically within the maximum tolerated dose. Optimal administration rates for a given set of conditions can be ascertained by those skilled in the art using conventional dosage administration tests.

The invention further provides a method of treating fibrillogenic diseases in a human subject. The method includes administering an amount of an indole-3-propionic acid or a salt or ester thereof effective to inhibit or reverse fibrillogenesis, i.e., inhibit or reverse fibril formation. As used herein, "fibrillogenic diseases" are meant to include any disease or condition involving the undesirable deposition of fibrils. As non-limiting examples thereof, such diseases or conditions include disorders or diseases resulting from abnormal formation of amyloid or amyloid-like deposits, such as, but not limited to, prion-related encephalopathies, Alzheimer's dementia or disease ("AD"), and other amyloidosis disorders. Examples of prion-related encephalopathies include Creutzfeldt-Jakob disease ("CJD") and Gerstmann-Straussler-Scheinker disease ("GSS") in humans, scrapie in sheep and goats, and spongiform encephalopathy in cattle.

The present invention further provides a method of treating diseases or other conditions where free radicals and/or oxidative stress play a role. The method includes administering an amount of an indole-3-propionic acid or a salt or ester thereof effective to treat the disease or condition. Diseases or conditions where free radicals and/or oxidative stress play a role include, without limitation, Parkinson's Disease, Lewy body dementia, amyotrophic lateral sclerosis, progressive supranuclear palsy, emphysema, and some forms of cancer.

Since indole-3-propionic acid and-salts and esters thereof are effective in treating diseases or other conditions where free radicals and/or oxidative stress play a role as well as preventing cytotoxic effects of amyloid beta protein on cells, these compounds are expected to be particularly useful in treating diseases associated with the amyloid beta protein, such as AD.

For all of the indications of indole-3-propionic acid or a salt or ester thereof, suitable dosage amounts are discussed above, and suitable routes of administration include. systemic administration (particularly in cases where the indole-3-propionic acid or a salt or ester thereof employed is one which crosses the blood-brain barrier). Systemic administration includes parenteral and oral administration, for example, as discussed in further detail below.

The indole-3-propionic acid or a salt or ester thereof can be administered alone or in combination with compatible carriers as a composition. Compatible carriers include suitable pharmaceutical carriers or diluents. The diluent or carrier ingredients should be selected so that they do not diminish the therapeutic effects of the indole-3-propionic acid or a salt or ester thereof as used in the present invention.

The compositions may be made up in any suitable form appropriate for the desired use; e.g., oral, parenteral, or topical administration. Suitable dosage forms for oral use include tablets, dispersible powders, granules, capsules, suspensions, syrups, elixirs, and skin patches. Inert diluents and carriers for tablets include, for example, calcium carbonate, . sodium carbonate, lactose, and talc. Tablets may also contain granulating and disintegrating agents such as starch and alginic acid, binding agents such as starch, gelatin, and acacia, and lubricating agents such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, for example, methyl cellulose, tragacanth, sodium alginate; wetting agents, such as lecithin and polyoxyethylene stearate; and preservatives, e.g., ethyl-p-hydroxybenzoate.

Dosage forms suitable for parenteral administration include solutions, suspensions, dispersions, emulsions, and the like. They may also be manufactured in the form of sterile solid compositions which can be dissolved or suspended in sterile injectable medium immediately before use. They may contain suspending or dispersing agents known in the art. Examples of parenteral administration are intraventricular, intracerebral, intramuscular, intravenous, intraperitoneal, rectal, and subcutaneous administration.

The present invention also relates to a method of decreasing oxidation in a biological sample. Examples of the types of oxidations that can be decreased using this method include lipid peroxidation and oxidations that are mediated by oxygen free-radical processes. The biological sample can be, for example, a cell or a group of cells, e.g. a tissue. The biological sample is contacted with an indole-3-propionic acid or a salt or ester thereof, such as the ones described above. Contacting can be carried out using any suitable method. For example, the indole-3-propionic acid or a salt or ester thereof can be delivered to the extracellular environment surrounding the biological sample. Alternatively, the indole-3-propionic acid or a salt or ester thereof-can be introduced directly into a cell, for example, by microinjection. The amount of indole-3-propionic acid or a salt or ester thereof effective to decrease oxidative processes can be determined by conventional methods, such as by delivering varying amounts of the indole-3-propionic acid or a salt or ester thereof and monitoring the concentration of the products of oxidation, such as oxygen free-radicals or the products of lipid peroxidation.

The present invention will be better understood with respect to the following non-limitative examples.

EXAMPLE 1

Tests were conducted to determine whether IPA had neuroprotective activity against the Alzheimer's amyloid peptide ("Aβ"). Widespread cerebral deposition of this 40–43 amino acid peptide causes extensive degeneration and death of neurons in Alzheimer's Disease.

To illustrate the cytoprotective affects of IPA against the cytotoxic effects of Aβ, cells of the human neuroblastoma cell line SK-N-SH were used. These cells were exposed to 50 μM Aβ (25–35), the actively toxic fragment of Aβ (Yankner et al., 1990) with or without 50 μM of IPA. As a control, the experiments were repeated without Aβ. As a positive control, the well-known anti-oxidant, phenyl-N-t-butylnitrone ("PBN") was substituted for IPA.

The results are shown in FIG. 1 as a bar graph illustrating viabilities-expressed as percent-ages. While Aβ alone has a pronounced cytotoxic effect on the cells, both IPA and PBN have strong protective activity.

EXAMPLE 2

Figure 2:
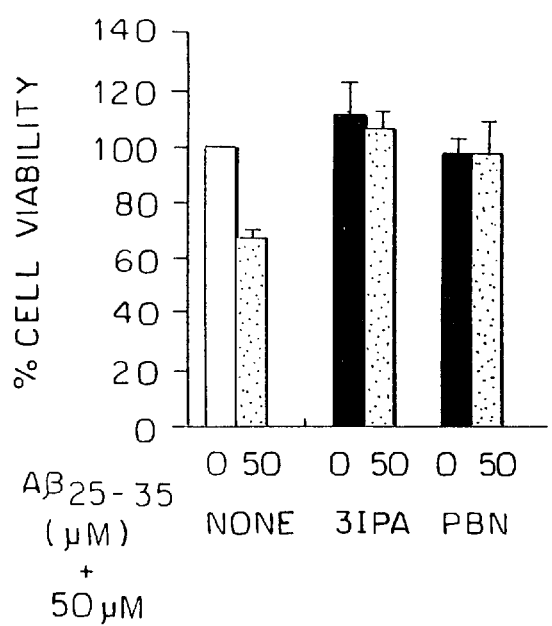
FIG. 2 is a bar graph illustrating viabilities expressed as percentages using PC12 rat pheochromocytoma cells exposed to either Aβ(25–35) alone or in conjunction with IPA or PBN.

The experiment of Example 1 was repeated using PC12 rat pheochromocytoma cells. The results are shown in FIG. 2 and are essentially identical to the results depicted in FIG. 1.

EXAMPLE 3

Figure 3:
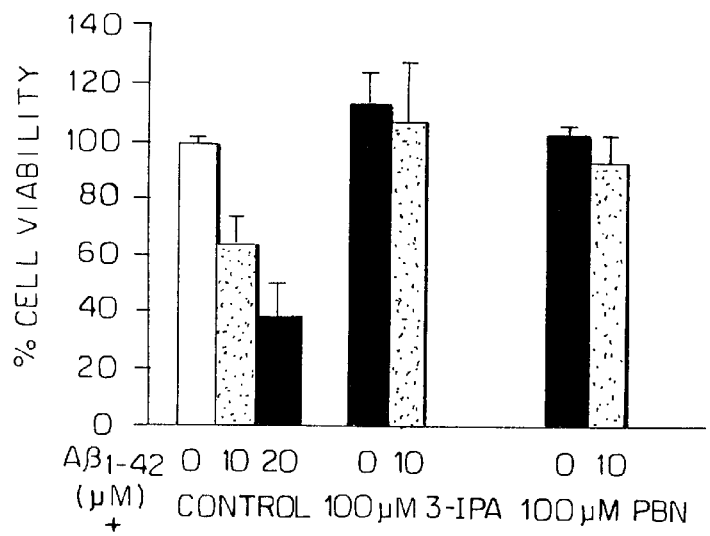
FIG. 3 is a bar graph illustrating viabilities expressed as percentages using SK-N-SH human neuroblastoma cells exposed to either Aβ(1–42) alone or in conjunction with IPA or PBN.

The experiment of Example 1 was repeated using the Aβ (1–42) peptide using the SK-N-SH human neuroblastoma cell line. The results are shown in FIG. 3 and are consistent with those shown with respect to Example 1.

EXAMPLE 4

Figure 4:
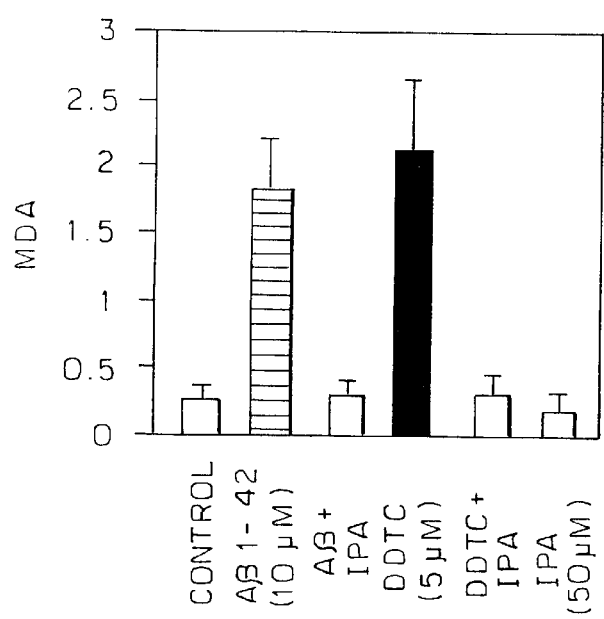
FIG. 4 is a bar graph illustrating the degree of lipid peroxidation (MDA measurement) induced by exposing cells to either amyloid peptide Aβ(1–42) or DDTC alone or each along with IPA.

In order to investigate the possibility that the cytoprotective properties of IPA are also the result, at least in part, of anti-oxidant activity, the -levels of malondialdehyde ("MDA"), a marker of lipid peroxidation, in PC12 cells exposed to Aβ or to oxidative stress were examined. Oxidative stress was delivered by exposing cells to diethyldithiocarbonate ("DDTC"), an inhibitor of superoxide dismutase and an established model of oxidative injury. The PC12 cells were exposed to either amyloid peptide alone or amyloid peptide along with IPA. In other experiments, the cells were exposed to either DDTC alone or DDTC with IPA. The results are shown in FIG. 4. It can be seen that IPA significantly decreases the production of malondialdehyde in treated cells, indicating that IPA has anti-oxidant activity. FIG. 4 shows both the neuroprotective and the anti-oxidant activities of IPA.

EXAMPLE 5

Figure 5:
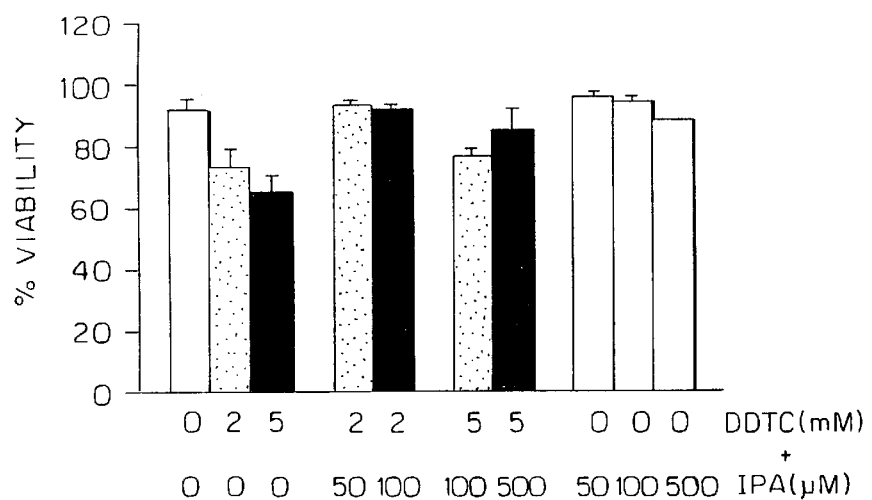
FIG. 5 is a bar graph showing the antioxidant activity of IPA by preventing cell death of PC12 rat neuroblastoma cells induced by inhibition of superoxide dismutase by DDTC.

To further confirm the observations shown in Example 4, we studied whether IPA was effective in preventing death of cells exposed to oxidative stress (DDTC). PC12 neuroblastoma cells were treated with varying amounts of DDTC, with or without varying amounts of IPA. The results are shown in FIG. 5. The anti-oxidant activity of IPA is shown by preventing cell death of neurblastoma cells induced by inhibition of the superoxide dismutase by DDTC. This is in agreement with the previously presented data that IPA increases the survival of cells exposed to DDTC.

EXAMPLE 6

Figure 6A:
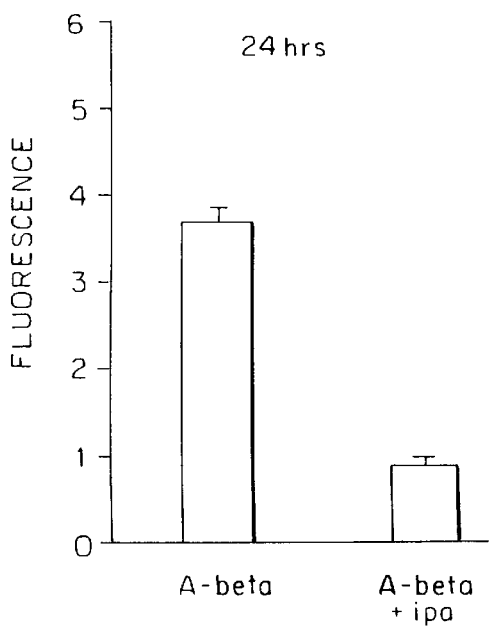
FIGS. 6A and 6B are bar graphs showing the effect of IPA on β sheet formation upon incubation of Aβ(1–40) for 24 hours (FIG. 6A) and 48 hours (FIG. 6B).
Figure 6B:
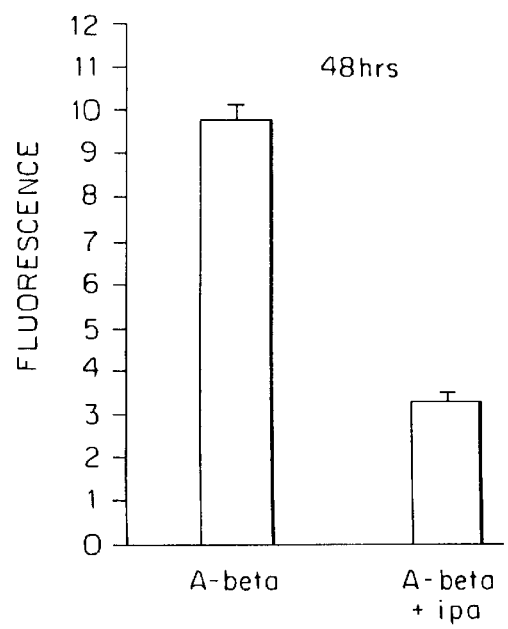

To determine whether IPA had an effect on AP fibrillogenesis, 150 μM Aβ (1–40) was incubated with 300 μM IPA, sodium salt, dissolved in ultrapure water (i.e., distilled, filtered, and sterilized) at a pH of 7. As a control, the ultrapure water used to dissolve the IPA containing an equivalent amount of sodium chloride was added to 150 μM Aβ (1–40) at a pH of 7. In one experiment, each of the solutions (i.e., the solution containing IPA and the control solution) was incubated for 24 hours. In a second experiment, each of the solutions was incubated for 48 hours. At the end of each incubation period, 50 mM glycine-NaOH buffer (pH 9.2) containing 2 μM thioflavin T was added to each sample (5 μL) to a final volume of 2 mL. Fluorescence, which is a direct measure of β sheet formation, was measured at an excitation wavelength of 435 nm and an emission wavelength of 485 nm using a Hitachi F-2000 fluorescence spectrometer. The average and standard deviations of the mean of 3 samples per condition were determined, and the results are presented (as bar graphs) in FIG. 6A (24 hour incubation) and FIG. 6B (48 hour incubation). In both the 24 and 48 hour incubation experiments, the amount of fluorescence is significantly less in the samples containing IPA (labeled A-beta+ipa) relative to control (labeled A-beta). This indicates that less β sheet formation occurred in the samples containing IPA relative to control, which, in turn, indicates that IPA is antifibrillogenic.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

References

Anderson, J. P., et al., Neurosci Lett 128:126–129 (1991).
Behl, C., et al., Biochem Biophys Res Commun 186:944-950 (1992).
Behl, C., et al., Brain Res 645:253–264 (1994).
Behl, C., et al., Cell 77:817–827 (1994).
Burdick, D., et al., J Biol Chem 267:546–554 (1992).
Busciglio, J., et al., Neurobiol Aging 13:609–612 (1992).
Busciglio, J., et al., J Neurochem 61(4):1565–1568 (1993).
Butterfield, D. A., et al., Biochem Biophys Res Commun 200:710–715 (1994).
Chartier-Harlin, M. C., et al., Nature 353(6347):844–846 (1991).
Copani, A., et al., Molecular Pharmacology 47(5):890-897 (1995).
Furuta, A., et al., Am J Pathol 146:357–367 (1995).
Glenner, G. G., and Wong, C. W., Biochem Biophys Res Commun 120:885–890 (1984).
Goodman, Y., and Mattson, M. P., Exp Neurol 128:1–12 (1994).
Haass, C., et al., Nature 359:322–324 (1992).
Harris, M. E., et al., Experimental Neurol 131:193–202 (1995).
Hensley, K., et al., Proc Natl Acad Sci USA 91(8): 3270–3274 (1994).

Johnson, H. E., and Crosby, D. G., J Org Chem, 25:569ff (1969)
Kemp, D. S., and Vellaccio, F., eds., *Organic Chemistry*, Worth Publishers, Inc., pp. 371–377 and 1258 (1980)
Kennedy, A. M., et al., Brain 116:309–324 (1993).
Le,.W-D., et al;, Brain Res 686:49–60 (1995).
Mark, R. J., et al., J Neurosci 15:6239–6249 (1995).
Mattson, M. P., Ann N.Y. Acad Sci 747:50–76 (1994).
Mattson, M. P., et al., Trends Neurosci 16:409–414 (1993).
Mattson, M. P., et al., J Neurosci 12:376–389 (1992).
Pappolla, M. A., et al., Am J Pathol 140:621–628 (1992).
Pappolla, M. A., and Robakis, N. K., In: *Perspectives in behavioural medicine, Alzheimers disease and AIDS*. Eds Stein, M., and Baum, M., Academic Press, San Diego, Calif., pp. 3–20 (1995).
Pappolla, M. A., et al., Mol Chem Neuropathol 28:21–34 (1996).
Pike, C. J., et al., J Neurosci 13:1676–1687 (1993).
Robakis, N. K., and Pangalos, M. N., Neurobiol Aging 15:S127–129 (1994).
Robakis, N. K., et al., Proc Natl Acad Sci USA 84:4190-4194 (1987).
Sambamurti, K., et al., J Neurosci Res 33:319–329 (1992).
Shoji, M., et al., Science 258:126–129 (1992).
Smith, M. A., et al., Amer J Pathol 145:42–47 (1994).
Tsuzuki et al., Biochem Pharmacol, 41:R5–8 (1991).
Weidemann, A., et al., Cell 57:115–126 (1989).
Weiss, J. H., et al., J Neurochem 62(1):372–375 (1994).
Yankner, D. A;, et al., Science250:279–282 (1990).
Zhang, Z., et al., Neurosci Lett 177:162–164 (1994).

What is claimed:

1. A method of preventing a cytotoxic effect of amyloid beta protein on cells comprising:
    exposing the cells to an effective amount of an indole-3-propionic acid or a salt or ester thereof.

2. A method according to claim 1, wherein the cytotoxic effect is cell death.

3. A method according to claim 1, wherein the cytotoxic effect is increased lipid peroxidation.

4. A method according to claim 1, wherein the cytotoxic effect is increased intracellular $Ca^{2+}$.

5. A method according to claim 1, wherein the cytotoxic effect is increased oxygen free-radicals.

6. A method according to claim 1, wherein the cells are neuronal cells.

7. A method according to claim 1, wherein the cells are present in a human subject and wherein said exposing comprises:
    administering the indole-3-propionic acid or salt or ester thereof systemically.

8. A method according to claim 1, wherein the cells are present in a human subject having a fibrillogenic disease.

9. A method of treating a fibrillogenic disease in a human subject comprising:
    administering an amount of an indole-3-propionic acid or a salt or ester thereof effective to prevent or reverse fibrillogenesis in the human subject.

10. A method according to claim 9, wherein said administering is carried out systemically.

11. A method according to claim 9, wherein the fibrillogenic disease is Alzheimer's Disease.

12. A method according to claim 9, wherein the fibrillogenic: disease is a prion-related encephalopathy.

13. A method of decreasing oxidation in a biological sample comprising:
    contacting the biological sample with an effective amount of an indole-3-propionic acid or a salt or ester thereof.

14. A method according to claim 13, wherein the biological sample is a cell.

15. A method according to claim 13, wherein said decreasing oxidation results in decreasing lipid peroxidation.

16. A method according to claim 13, wherein said decreasing oxidation results in decreasing oxygen free-radicals.

17. A method for treating diseases or other conditions where free radicals and/or oxidative stress contribute to the pathogenesis, comprising:
    administering to a patient in need of such treatment an amount of an indole-3-propionic acid or a salt or ester thereof effective for the treatment of said disease or condition.

18. A method according to claim 17, wherein said administering is carried out systemically.

19. A method according to claim 17, wherein the disease or other condition is selected from the group consisting of Parkinson's Disease, Lewy body dementia, amyotrophic lateral sclerosis, progressive supranuclear palsy, stroke, atherosclerosis, emphysema, and a cancer whose pathogenesis is contributed to by free radicals and/or oxidative stress.

* * * * *